(12) United States Patent
Sierra et al.

(10) Patent No.: US 8,641,631 B2
(45) Date of Patent: Feb. 4, 2014

(54) NON-INVASIVE MONITORING OF RESPIRATORY RATE, HEART RATE AND APNEA

(75) Inventors: Gilberto Sierra, Montreal (CA); Victor F. Lanzo, Laval (CA); Valery Telfort, Montreal (CA)

(73) Assignee: Masimo Corporation, Irvine, CA (US)

( * ) Notice: Subject to any disclaimer, the term of this patent is extended or adjusted under 35 U.S.C. 154(b) by 1305 days.

(21) Appl. No.: 11/547,570

(22) PCT Filed: Apr. 8, 2005

(86) PCT No.: PCT/CA2005/000536
§ 371 (c)(1),
(2), (4) Date: Jun. 19, 2007

(87) PCT Pub. No.: WO2005/096931
PCT Pub. Date: Oct. 20, 2005

(65) Prior Publication Data
US 2007/0282212 A1    Dec. 6, 2007

Related U.S. Application Data

(60) Provisional application No. 60/560,277, filed on Apr. 8, 2004.

(30) Foreign Application Priority Data

Apr. 8, 2004    (CA) ...................................... 2464029

(51) Int. Cl.
*A61B 5/02*    (2006.01)
(52) U.S. Cl.
USPC ........................................................ 600/483
(58) Field of Classification Search
USPC ................................................ 600/529–543
See application file for complete search history.

(56) References Cited

U.S. PATENT DOCUMENTS

| 3,682,161 A | 8/1972 | Alibert |
| 4,127,749 A | 11/1978 | Atoji et al. |

(Continued)

FOREIGN PATENT DOCUMENTS

| CA | 2262236 | 4/2008 |
| EP | 0716628 | 12/1998 |

(Continued)

OTHER PUBLICATIONS

U.S. Appl. No. 12/904,775, filed Oct. 14, 2010, Fechter et al.

(Continued)

*Primary Examiner* — Patricia Mallari
*Assistant Examiner* — Vasuda Ramachandran
(74) *Attorney, Agent, or Firm* — Knobbe, Martens, Olson & Bear LLP

(57) ABSTRACT

A method and apparatus for estimating a respiratory rate of a patient. The method comprises the steps of recording respiratory sounds of the patient, deriving a plurality of respiratory rates from the recorded sounds using a plurality of respiratory rate estimating methods and applying a heuristic to the plurality of derived respiratory rates, the heuristic selecting one of the derived respiratory rates. The selected respiratory rate is the estimated respiratory rate. The apparatus comprises at least one sensor recording respiratory sounds of the patient, a plurality of respiratory rate processors, each of the processors comprising a respiratory rate calculating method, a heuristic means for selecting one of the calculated respiratory rates and a display means for displaying the selected respiratory as the estimated respiratory rate.

37 Claims, 9 Drawing Sheets

(56) References Cited

U.S. PATENT DOCUMENTS

| | | | |
|---|---|---|---|
| 4,326,143 A | 4/1982 | Guth et al. | |
| 4,537,200 A | 8/1985 | Widrow | |
| 4,884,809 A | 12/1989 | Rowan | |
| 4,958,638 A * | 9/1990 | Sharpe et al. | 600/407 |
| 4,960,128 A | 10/1990 | Gordon et al. | |
| 4,964,408 A | 10/1990 | Hink et al. | |
| 5,033,032 A | 7/1991 | Houghtaling | |
| 5,041,187 A | 8/1991 | Hink et al. | |
| 5,069,213 A | 12/1991 | Polczynski | |
| 5,143,078 A * | 9/1992 | Mather et al. | 600/529 |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,302 A * | 12/1994 | Tsiang | 704/235 |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,448,996 A | 9/1995 | Bellin et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| 5,724,983 A | 3/1998 | Selker et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,819,007 A | 10/1998 | Elghazzawi | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,865,736 A | 2/1999 | Baker, Jr. et al. | |
| 5,890,929 A | 4/1999 | Mills et al. | |
| 5,904,654 A | 5/1999 | Wohltmann et al. | |
| 5,919,134 A | 7/1999 | Diab | |
| 5,928,156 A | 7/1999 | Krumbiegel et al. | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,029,665 A | 2/2000 | Berthon-Jones | |
| 6,036,642 A | 3/2000 | Diab et al. | |
| 6,045,509 A | 4/2000 | Caro et al. | |
| 6,064,910 A | 5/2000 | Andersson et al. | |
| 6,067,462 A | 5/2000 | Diab et al. | |
| 6,081,735 A | 6/2000 | Diab et al. | |
| 6,083,172 A * | 7/2000 | Baker et al. | 600/500 |
| 6,088,607 A | 7/2000 | Diab et al. | |
| 6,110,522 A | 8/2000 | Lepper, Jr. et al. | |
| 6,124,597 A | 9/2000 | Shehada et al. | |
| 6,128,521 A | 10/2000 | Marro et al. | |
| 6,129,675 A | 10/2000 | Jay | |
| 6,138,675 A * | 10/2000 | Berthon-Jones | 128/204.23 |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,248,083 B1 | 6/2001 | Smith et al. | |
| 6,253,097 B1 | 6/2001 | Aronow et al. | |
| 6,254,551 B1 * | 7/2001 | Varis | 600/595 |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,443,907 B1 * | 9/2002 | Mansy et al. | 600/529 |
| 6,463,311 B1 | 10/2002 | Diab | |
| 6,470,199 B1 | 10/2002 | Kopotic et al. | |
| 6,486,588 B2 | 11/2002 | Doron et al. | |
| 6,491,647 B1 * | 12/2002 | Bridger et al. | 600/585 |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,517,497 B2 | 2/2003 | Rymut et al. | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,647,280 B2 * | 11/2003 | Bahr et al. | 600/323 |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |

(56) References Cited

U.S. PATENT DOCUMENTS

| | | | |
|---|---|---|---|
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,754,516 B2 | 6/2004 | Mannheimer |
| 6,760,607 B2 | 7/2004 | Al-Ali |
| 6,766,038 B1 | 7/2004 | Sakuma et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,581 B1 | 1/2005 | El-Solh et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,194,306 B1 * | 3/2007 | Turcott ............ 607/17 |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,398,115 B2 | 7/2008 | Lynn |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,539,533 B2 * | 5/2009 | Tran ............ 600/509 |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,690,378 B1 | 4/2010 | Turcott |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |

(56) References Cited

U.S. PATENT DOCUMENTS

| | | | |
|---|---|---|---|
| 7,941,199 B2 | 5/2011 | Kiani | |
| 7,951,086 B2 | 5/2011 | Flaherty et al. | |
| 7,957,780 B2 | 6/2011 | Lamego et al. | |
| 7,962,188 B2 | 6/2011 | Kiani et al. | |
| 7,962,190 B1 | 6/2011 | Diab et al. | |
| 7,976,472 B2 | 7/2011 | Kiani | |
| 7,988,637 B2 | 8/2011 | Diab | |
| 7,990,382 B2 | 8/2011 | Kiani | |
| 7,991,446 B2 | 8/2011 | Ali et al. | |
| 8,000,761 B2 | 8/2011 | Al-Ali | |
| 8,008,088 B2 | 8/2011 | Bellott et al. | |
| RE42,753 E | 9/2011 | Kiani-Azarbayjany et al. | |
| 8,019,400 B2 | 9/2011 | Diab et al. | |
| 8,028,701 B2 | 10/2011 | Al-Ali et al. | |
| 8,029,765 B2 | 10/2011 | Bellott et al. | |
| 8,036,728 B2 | 10/2011 | Diab et al. | |
| 8,046,040 B2 | 10/2011 | Ali et al. | |
| 8,046,041 B2 | 10/2011 | Diab et al. | |
| 8,046,042 B2 | 10/2011 | Diab et al. | |
| 8,048,040 B2 | 11/2011 | Kiani | |
| 8,050,728 B2 | 11/2011 | Al-Ali et al. | |
| RE43,169 E | 2/2012 | Parker | |
| 8,126,528 B2 | 2/2012 | Diab et al. | |
| 8,128,572 B2 | 3/2012 | Diab et al. | |
| 8,130,105 B2 | 3/2012 | Al-Ali et al. | |
| 8,145,287 B2 | 3/2012 | Diab et al. | |
| 8,150,487 B2 | 4/2012 | Diab et al. | |
| 8,175,672 B2 | 5/2012 | Parker | |
| 8,180,420 B2 | 5/2012 | Diab et al. | |
| 8,185,180 B2 | 5/2012 | Diab et al. | |
| 8,190,223 B2 | 5/2012 | Al-Ali et al. | |
| 8,190,227 B2 | 5/2012 | Diab et al. | |
| 8,224,411 B2 | 7/2012 | Al-Ali et al. | |
| 8,228,181 B2 | 7/2012 | Al-Ali | |
| 8,229,533 B2 | 7/2012 | Diab et al. | |
| 8,255,028 B2 | 8/2012 | Al-Ali et al. | |
| 8,260,577 B2 | 9/2012 | Weber et al. | |
| 2001/0002206 A1 | 5/2001 | Diab et al. | |
| 2002/0193670 A1 | 12/2002 | Garfield et al. | |
| 2003/0015368 A1 | 1/2003 | Cybulski et al. | |
| 2003/0076494 A1* | 4/2003 | Bonin et al. | 356/336 |
| 2003/0158466 A1 | 8/2003 | Lynn et al. | |
| 2003/0163054 A1 | 8/2003 | Dekker | |
| 2004/0010202 A1 | 1/2004 | Nakatani | |
| 2004/0059203 A1 | 3/2004 | Guerrero | |
| 2004/0133087 A1 | 7/2004 | Ali et al. | |
| 2004/0158162 A1 | 8/2004 | Narimatsu | |
| 2006/0047215 A1 | 3/2006 | Newman et al. | |
| 2006/0149144 A1 | 7/2006 | Lynn et al. | |
| 2006/0155206 A1 | 7/2006 | Lynn | |
| 2006/0155207 A1 | 7/2006 | Lynn et al. | |
| 2006/0161071 A1 | 7/2006 | Lynn et al. | |
| 2006/0189880 A1 | 8/2006 | Lynn et al. | |
| 2006/0195041 A1 | 8/2006 | Lynn et al. | |
| 2006/0235324 A1 | 10/2006 | Lynn | |
| 2006/0238333 A1 | 10/2006 | Welch et al. | |
| 2007/0093721 A1 | 4/2007 | Lynn et al. | |
| 2007/0129643 A1* | 6/2007 | Kwok et al. | 600/529 |
| 2007/0129647 A1 | 6/2007 | Lynn | |
| 2007/0135725 A1* | 6/2007 | Hatlestad | 600/529 |
| 2007/0149860 A1 | 6/2007 | Lynn et al. | |
| 2007/0185397 A1 | 8/2007 | Govari et al. | |
| 2007/0282212 A1 | 12/2007 | Sierra et al. | |
| 2008/0039735 A1 | 2/2008 | Hickerson | |
| 2008/0076972 A1 | 3/2008 | Dorogusker et al. | |
| 2008/0161878 A1 | 7/2008 | Tehrani et al. | |
| 2009/0018429 A1 | 1/2009 | Saliga et al. | |
| 2009/0093687 A1 | 4/2009 | Telfort et al. | |
| 2009/0187065 A1 | 7/2009 | Basinger | |
| 2009/0299157 A1 | 12/2009 | Telfort et al. | |
| 2010/0274099 A1 | 10/2010 | Telfort et al. | |

FOREIGN PATENT DOCUMENTS

| | | |
|---|---|---|
| EP | 0659058 | 1/1999 |
| EP | 1207536 | 5/2002 |
| GB | 2358546 | 11/1999 |
| JP | 6214898 | 1/1987 |
| JP | 01-309872 | 6/1998 |
| JP | 10-155755 | 6/1998 |
| JP | 2001-50713 | 5/1999 |
| JP | 2003-329719 | 11/2003 |
| WO | WO 94/05207 | 3/1994 |
| WO | WO 94/13207 | 6/1994 |
| WO | WO 95/29632 | 11/1995 |
| WO | WO 99/53277 | 10/1999 |
| WO | WO 00/10462 | 3/2000 |
| WO | WO 01/34033 | 5/2001 |
| WO | WO 01/78059 | 10/2001 |
| WO | WO 01/97691 | 12/2001 |
| WO | WO 02/03042 | 1/2002 |
| WO | WO 03/058646 | 7/2003 |
| WO | WO 03/087737 | 10/2003 |
| WO | WO 2004/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |

OTHER PUBLICATIONS

U.S. Appl. No. 12/904,789, filed Oct. 14, 2010, Telfort, Valery et al.
U.S. Appl. No. 12/904,823, filed Oct. 14, 2010, Al-Ali et al.
U.S. Appl. No. 12/904,836, filed Oct. 14, 2010, Al-Ali, Ammar.
U.S. Appl. No. 12/904,890, filed Oct. 14, 2010, Telfort et al.
U.S. Appl. No. 12/904,907, filed Oct. 14, 2010, Telfort et al.
U.S. Appl. No. 12/904,931, filed Oct. 14, 2010, Telfort et al.
U.S. Appl. No. 12/904,938, filed Oct. 14, 2010, Telfort et al.
U.S. Appl. No. 12/905,036, filed Oct. 14, 2010, Kiani et al.
U.S. Appl. No. 12/905,384, filed Oct. 15, 2010, Al-Ali et al.
U.S. Appl. No. 12/905,449, filed Oct. 15, 2010, Al-Ali et al.
U.S. Appl. No. 12/905,489, filed Oct. 15, 2010, Weber et al.
U.S. Appl. No. 12/905,530, filed Oct. 15, 2010, Al-Ali et al.
U.S. Appl. No. 12/960,325, filed Dec. 3, 2010, Al-Ali Ammar et al.
Analog Devices, 12-Bit Serial Input Multiplying D/A Converter, Product Data Sheet, 2000.
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report, PCT Application PCT/CA2003/000536, Dec. 11, 2003; 2 pages.
International Search Report, PCT Application PCT/US2009/069287, Mar. 30, 2010; 7 pages.
Welch Allyn, ECG ASIC, Product Data Sheete, 2001.
Sierra et al., Monitoring Respiratory Rate Based on Tracheal Sounds. First Experieances, Proceedings of the 26th Annual Int'l Conf. of the IEEE EMBS (Sep. 2004), 317-320.
Japanese Office Action for JP Application No. 2007-506626 mailed Mar. 4, 2011.
Supplementary Partial European Search Report for International Application No. 05732095.4, dated Jun. 26, 2009 in 4 pages.
International Search Report and Written Opinion issued in application No. PCT/US2010/052756 on Feb. 6, 2012.
Chambrin, M-C.; "Alarms in the intensive care unit: how can the Number of false alarms be reduced?", Critical Care Aug. 2001, vol. 5 No. 4; p. 1-5.
Watt, R. C.; "Alarms and Anesthesia. Challenges in the design of Intelligent systems for Patient Monitoring"; IEEE Engineering in Medicine and biology; Dec. 1993, p. 34-41.
Eldor et al., "A device for monitoring ventilation during anaesthesia; the paratracheal audible respiratory monitor", Canadian Journal of Anaesthesia, 1990, vol. 9, No. 1, p. 95-98.

* cited by examiner

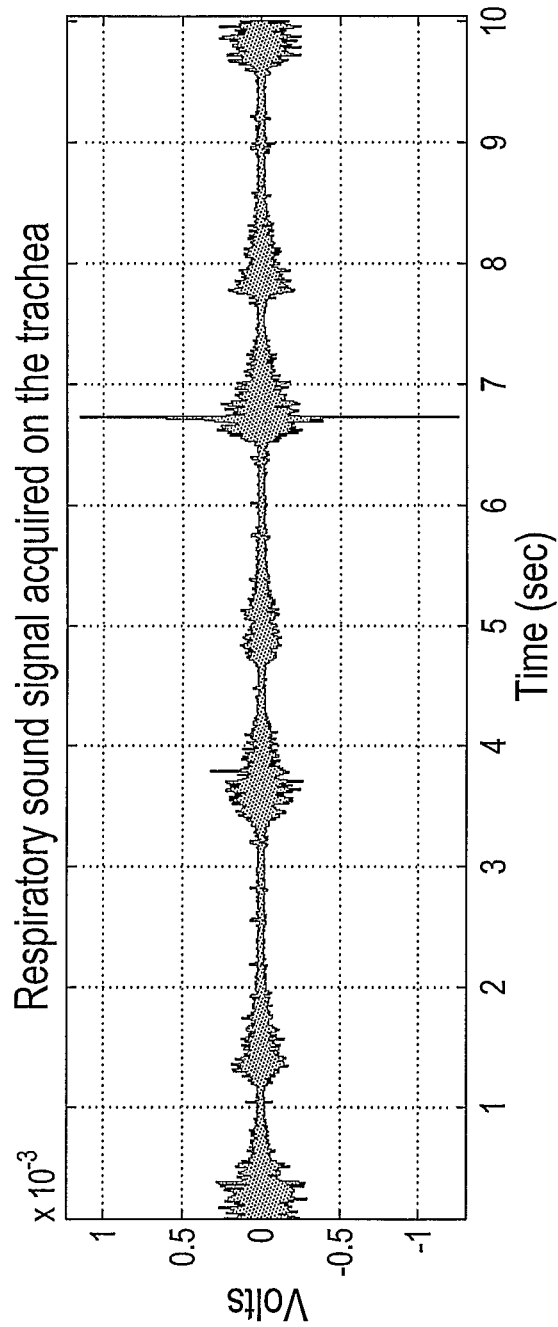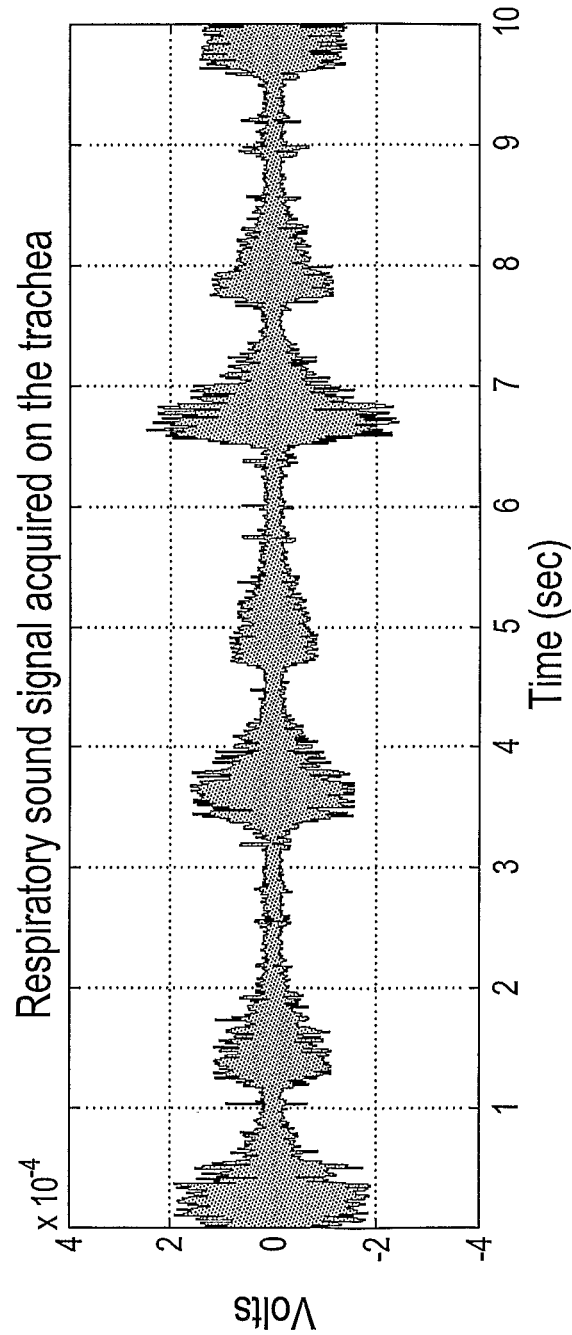

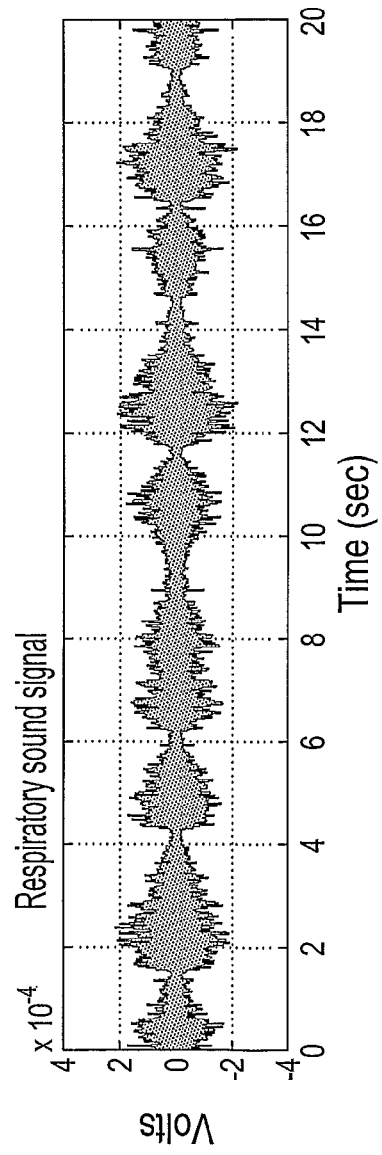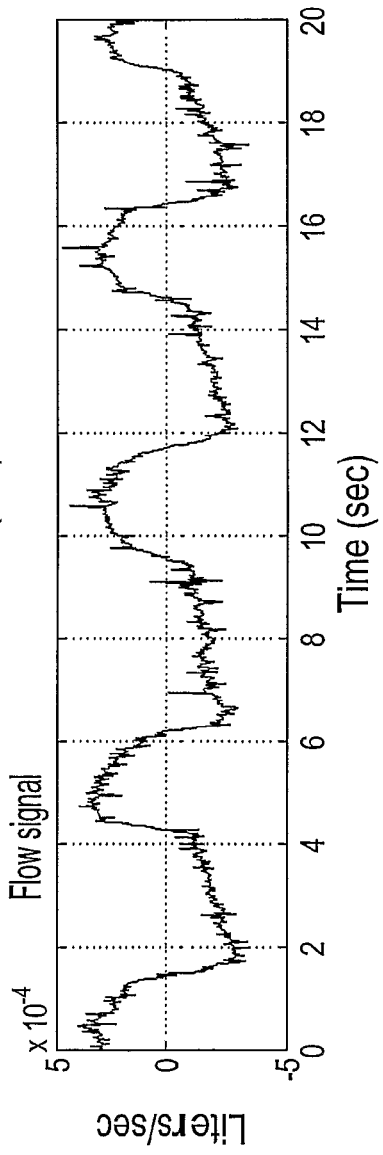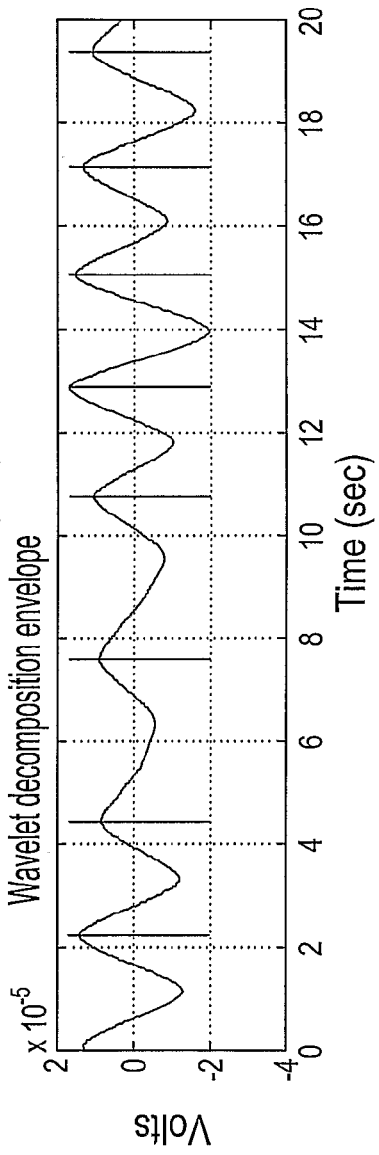

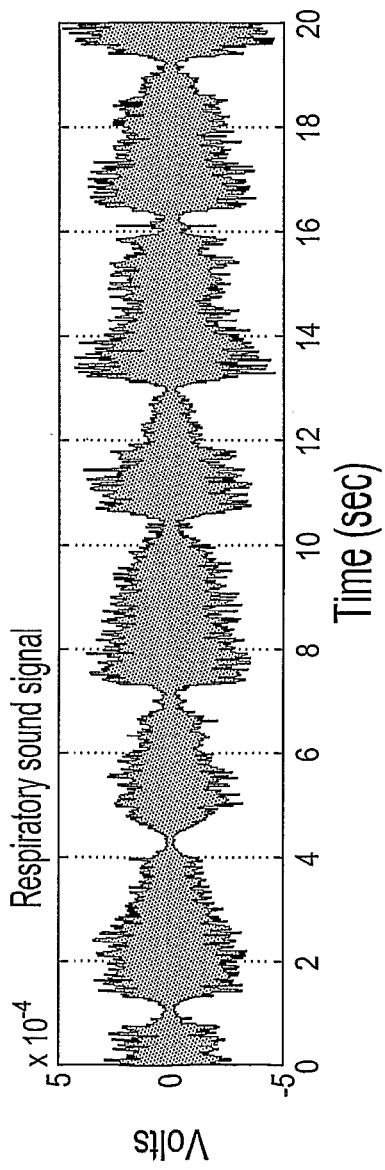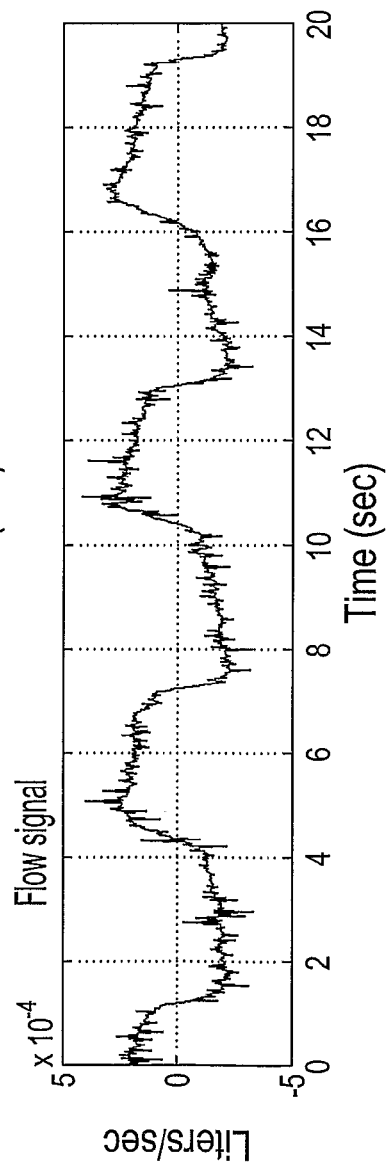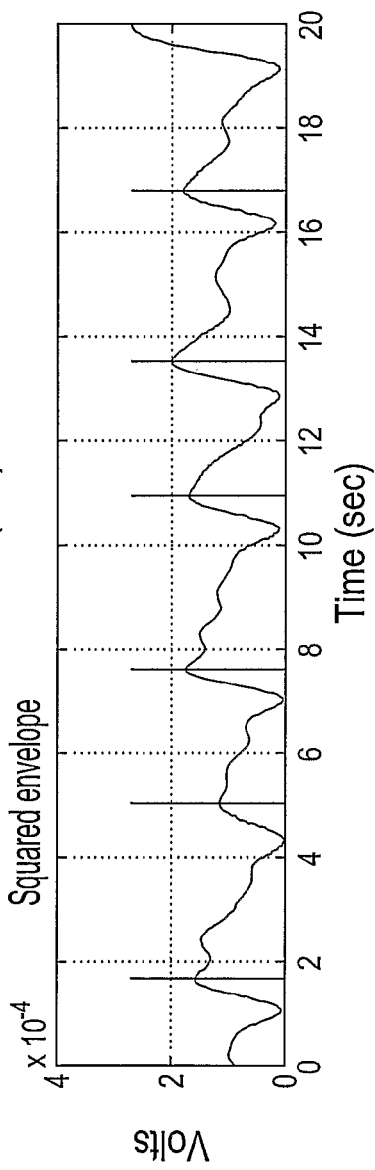
Fig. 6A
Fig. 6B
Fig. 6C

NON-INVASIVE MONITORING OF RESPIRATORY RATE, HEART RATE AND APNEA

This application is the national stage of International Application No. PCT/CA2005/000536, filed Apr. 8, 2005, which claims the benefit of and priority from U.S. Provisional No. 60/560,277, filed Apr. 8, 2004, which are incorporated by reference herein.

FIELD OF THE INVENTION

The present invention relates to a method and apparatus for the non-invasive monitoring of respiratory rate, heart rate and apnea. In particular, the present invention relates to a method for determining respiratory rate by combining the results of a plurality of respiratory rate estimation methods and selecting a preferred rate using a heuristic, and an apparatus implementing the same.

BACKGROUND OF THE INVENTION

Respiratory Rate

Respiratory failure can become a life-threatening condition in a few minutes or be the result of a build up over several hours. Respiratory failure is very difficult to predict, and as a result continuous monitoring of respiratory activity is typically necessary in clinical, high-risk situations. Appropriate monitoring equipment can be life-saving (see Folke M, Cernerud A, Ekstrom M, Hok B; Critical Review of Non-invasive Respiratory Monitoring in Medical Care; Medical & Biological Engineering & Computing 2003, Vol 41, pp. 377-383).

Numerous studies have shown that Respiratory Rate (RR) provides one of the most accurate markers for indicating acute respiratory dysfunction, and thus is used to track the progress of patients in intensive care or post-operative care or anyone with potentially unstable respiration (see Krieger B, Feinerman D, Zaron A, Bizousky F; *Continuous Noninvasive Monitoring of Respiratory Rate in Critically Ill Patients*; Chest/90/5/November, 1986, pp 632-634, Browning I B, D'Alonzo G E, Tobin M J; *Importance of Respiratory Rate as an Indicator of Respiratory Dysfunction in Patients with Cystic Fibrosis*; Chest/97/6/June 1990, pp 1317-1321, Gravelyn T R, Weg J G; *Respiratory Rate as an Indicator of Acute Respiratory Dysfunction*; JAMA, Sep. 5, 1980—Vol 244, No. 10, pp 1123-1125).

RR has also been shown to be a very accurate marker for weaning outcomes for ventilated patients (see Tobin M J, Perez W, Guenther M, Semmes B J, Mador J, Allen S J, Lodato R F, Dantzker D R; *The Pattern of Breathing during Successful and Unsuccessful Trials of Weaning from Mechanical Ventilation*; AM Rev Respir DIS 1986; 134: 1111-1118 and El-Khatib M. Jamaleddine G, Soubra R, Muallem M; *Pattern of Spontaneous Breathing: Potential Marker for Weaning Outcome*, Spontaneous Breathing Pattern and Weaning from Mechanical Ventilation; Intensive Care Med (2001) 27:52-68) as it exhibits high correlation with both the success and failure of extubations.

During sedation, monitoring of the RR has been shown to be a more rapid marker of the induction of anesthesia than any other clinical measure, such as lash reflex, loss of grip, cessation of finger tapping, and loss of arm tone (see Strickland T L, Drummond G B; *Comparison of Pattern of Breathing with Other Measures of Induction of Anesthesia, Using Propofol, Methohexital, and Servoflurane*; British Journal Of Anesthesia, 2001, Vol. 86, No. 5, pp 639-644). During conscious sedation (narcotic sedation), there is always a risk of respiratory depression. However, monitoring of the respiratory pattern combined with pulse oximetry yield the most useful information about the occurrence of respiratory depression and changes in RR typically provide an earlier warning than does pulse oximetry or end-tidal $CO_2$ tension (see Shibutani K, Komatsu T. Ogawa T, Braatz T P, Tsuenekage T; *Monitoring of Breathing Intervals in Narcotic Sedation*; International Journal of Clinical Monitoring & Computing; 8: 159-162, 1991).

Respiration monitoring is also useful during non critical care, e.g. during exercise testing and different types of cardiac investigations. In the latter case there is also need to time the different phases of respiration, since the heart function is modulated by respiration. A forthcoming area of application for respiration monitoring may be that of home-care (see Hult P, et al., *An improved bioacoustic method for monitoring of respiration*. Technology and Health Care 2004; 12: 323-332).

Despite the obvious benefits of performing continuous respiratory monitoring, the search for an accurate, non-invasive, and non-obtrusive method to continuously monitor RR has proven to be long and unsuccessful. Several technologies have been developed in an attempt to fill this clinical gap, but none has gained sufficient physician confidence to become a standard of care. In this regard, inductive plethysmography, fiber optic humidification and capnography are among the most popular technologies. Each of these has advantages and disadvantages, but none has proven to be clearly superior. More suitable technologies are still needed to address such issues as: low signal to noise ratio, different breath sound intensities, phase duration, variable breathing patterns, interferences from non-biological sounds (electromagnetic interference, movement artifacts, environmental noise, etc.), and interference from biological sounds such as the heart seat, swallowing, coughing, vocalization, etc.

Tracheal sounds, typically heard at the suprasternal notch or at the lateral neck near the pharynx, have become of significant interest during the last decade. The tracheal sound signal is strong, covering a wider range of frequencies than lung sounds at the chest wall, has distinctly separable respiratory phases, and a close relation to airflow. Generally, the placement of a sensor over the trachea is relatively easy as there is less interference from body hair, garments, etc, as compared to chest-wall recording sites.

The generation of tracheal sounds is primarily related to turbulent air flow in upper airways, including the pharynx, glottis, and subglottic regions. Flow turbulence and jet formation at the glottis cause pressure fluctuations within the airway lumen. Sound pressure waves within the airway gas and airway wall motion are likely contributing to the vibrations that reach the neck surface and are recorded as tracheal sounds. Because the distance from the various sound sources in the upper airways to a sensor on the neck surface is relatively short and without interposition of lung tissue, tracheal sounds are often interpreted as a more pure, less filtered breath sound. Tracheal sounds have been characterized as broad spectrum noise, covering a frequency range of less than 100 Hz to more than 1500 Hz, with a sharp drop in power above a cutoff frequency of approximately 800 Hz. While the spectral shape of tracheal sounds varies widely from person to person, it is quite reproducible within the same person. This likely reflects the strong influence of individual airway anatomy.

Pulmonary clinicians are interested in tracheal sounds as early indicators of upper airway flow obstruction and as a source for quantitative as well as qualitative assessments of ventilation. Measurements of tracheal sounds provide valuable and in some cases unique information about respiratory health.

Apnea

Apnea monitoring by simple acoustical detection of tracheal sounds is an obvious application and has been successfully applied in both adults and in children. The detection of apneic events are a normal derivative from the RR estimation. A temporary cessation in breathing, typically lasting at least 10 seconds in duration, is referred to as apnea. Longer pauses may be of sufficient duration to cause a fall in the amount of oxygen in the arterial blood, and have the potential to cause permanent organ damage, or, in the extreme case, death. Adults with sleep apnea are very susceptible to exacerbation of this condition post-surgery, and therefore their respiration must be carefully monitored. Disordered breathing during sleep is a common condition with an estimated prevalence of up to 24% in men and 9% in women in North America. It is associated with excessive morbidity and increased mortality from cardiovascular and cerebrovascular events and increased risk of road traffic accidents (see Young et al., *The occurrence of sleep-disordered breathing among middle-aged adults*, N Engl J Med 1993; 328: 1230-1235). The condition can be suspected clinically in the presence of classic symptoms such as snoring, daytime hyper-somnolence, obesity, and male gender. The diagnosis is typically confirmed by polysomnography. The most common sleep disorder is Obstructive Sleep Apnea Syndrome (OSAS), also known as Sleep Apnea Hypopnea Syndrome (SAHS). This condition is so much linked to excessive morbidity and mortality, that it is considered a public health hazard at par with smoking (see Findley et al., *Automobile accidents involving patients with obstructive sleep apnea*, Am Rev Respir Dis 1988; 138: 337-340).

Heart Rate

The rhythm of the heart in terms of beats per minute may be easily estimated on the tracheal site by counting the readily identifiable heart sound waves. Heart rate (HR) is altered by cardiovascular diseases and abnormalities such as arrhythmias and conduction problems. The main cause of death in developed countries is due to cardiovascular diseases and mostly they are triggered by an arrhythmic event (ventricular tachycardia or ventricular fibrillation). The HR is controlled by specialized pacemaker cells that form the sinoatrial (SA) node located at the junction of the superior vena cava and the right atrium. The firing rate of the SA node is controlled by impulses from the autonomous and central nervous system. It is now commonly accepted that the heart sounds are not caused by valve leaflet movement per se, as earlier believed, but by vibrations of the whole cardiovascular system triggered by pressure gradients (see Rangayyan R M, Biomedica, *Signal Analysis* 2002, IEEE Press Series, Wiley Inter-Science). The normal (resting) HR is about 70 bpm. The HR is slower during sleep, but abnormally low HR (below 60 bpm) during activity could indicate a disorder called bradycardia. The instantaneous HR could reach values as high as 200 bpm during vigorous exercise or athletic activity; a high resting HR could be due to illness, disease, or cardiac abnormalities, and is termed tachycardia.

SUMMARY OF THE INVENTION

In order to address the above and other drawbacks, there is provided a method for estimating a respiratory rate of a patient comprising the steps of recording respiratory sounds of the patient, deriving a plurality of respiratory rates from the recorded sounds using a plurality of respiratory rate estimating methods and applying a heuristic to the plurality of derived respiratory rates, the heuristic selecting one of the derived respiratory rates. The selected respiratory rate is the estimated respiratory rate.

There is also provided a method for signalling sleep apnea comprising the steps of the above method wherein when the estimated respiratory rate exceeds a predetermined interval an alarm is raised.

Furthermore, there is provided a method for estimating a respiratory rate of a patient. The method comprises the steps of recording respiratory sounds of the patient and determining silent intervals in the recorded sounds. The estimated respiratory rate is equivalent to a frequency of the silent intervals.

Additionally, there is provided an apparatus for providing an estimated respiratory rate of a patient. The apparatus comprises at least one sensor recording respiratory sounds of the patient, a plurality of respiratory rate processors, each of the processors comprising a respiratory rate calculating method, a heuristic means for selecting one of the calculated respiratory rates and a display means for displaying the selected respiratory as the estimated respiratory rate.

Also, there is provided an apparatus for signalling sleep apnea in a patient. The apparatus comprises at least one sensor recording respiratory sounds of the patient, a plurality of respiratory rate processors where each of the processors comprising a respiratory rate calculating methods, a heuristic means for selecting one of the calculated respiratory rates and an alarm. When the selected respiratory rate is slower than a predetermined rate, the alarm is activated.

Other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

In the appended drawings;

FIG. 3 is a graph of a respiratory sound signal showing artifacts (glitches) and with glitches removed according to an illustrative embodiment of the present invention;

FIG. 4 is a graph of a respiratory sound signal, flow signal and wavelet decomposition envelope according to an illustrative embodiment of the present invention;

FIG. 6 is a graph of a respiratory sound signal, flow signal and squared envelope according to an illustrative embodiment of the present invention;

DETAILED DESCRIPTION OF THE ILLUSTRATIVE EMBODIMENTS

Figure 1:
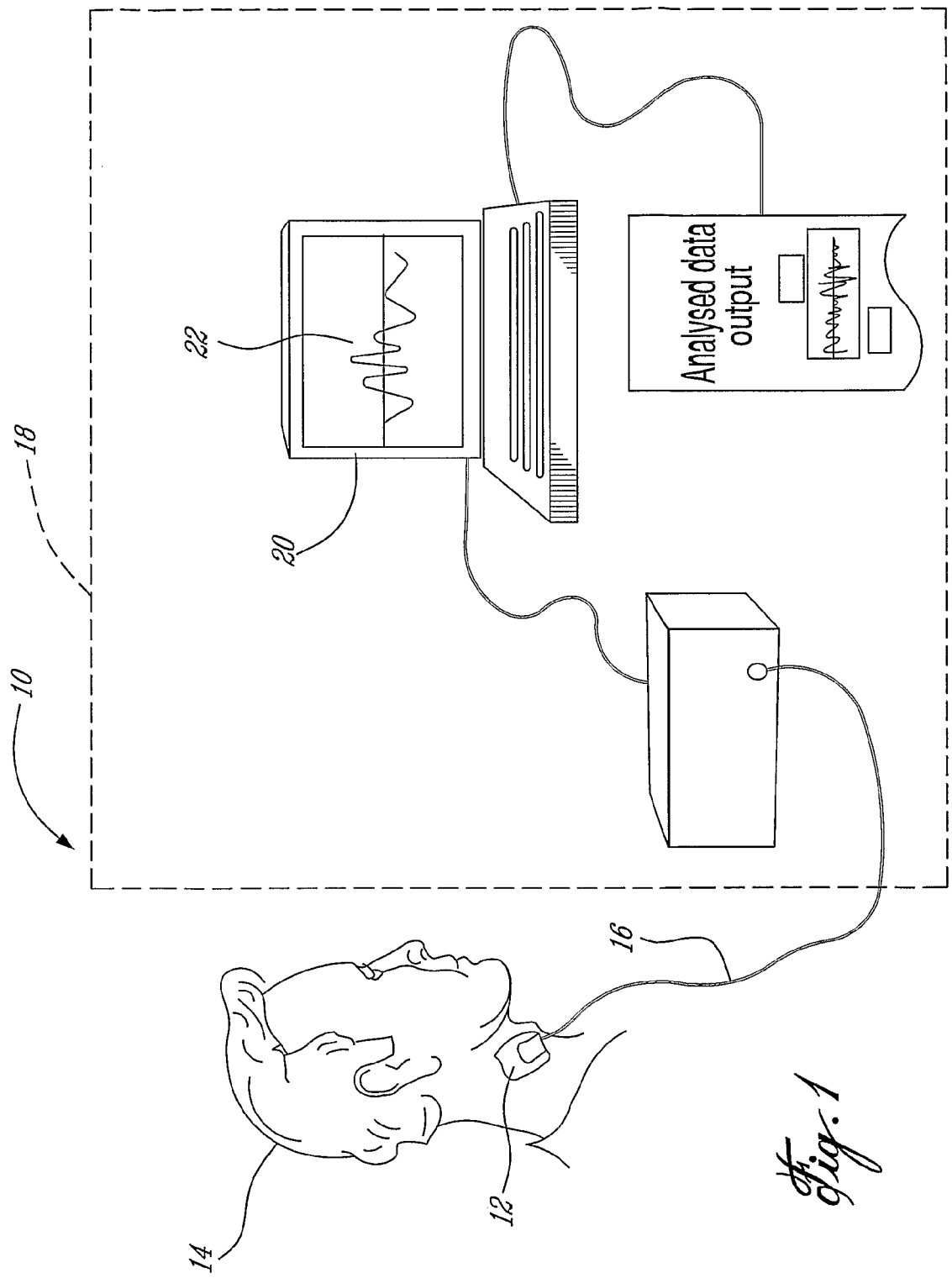
FIG. 1 is a front view of a patient with a sensor attached to monitor respiratory sounds according to an illustrative embodiment of the present invention.

Referring now to FIG. 1, a non-invasive respiratory rate, heart rate and apnea monitor, generally referred to using the reference numeral 10, will now be described. Biological sound sensors 12, illustratively identical and for example as those described in U.S. Pat. No. 6,661,161, detect the biological sounds and vibrations emanating from the throat of a patient 14 and produces an output electrical signal. Note that in a given embodiment, a single biological sound sensor as in 12 or more than one could also be used to detect biological sounds and vibrations. The signals are transferred via appropriate electrical leads 16 to a data acquisition system 18, which amplifies and filters the electrical signal prior to converting them into a digital format. Finally, the methods implemented in a computer 20 extract the physiological information from the data and display the results through a graphical user interface 22.

Acquisition System

The acquisition system comprises a Pentium based laptop computer running Windows 2000 and a multi-channel custom designed biosignal amplifier. The bandwidth of the sound channel(s) is selectable from 0 to 1500 Hz. A sampling frequency for the sound channel(s) was chosen and set at 3 kHz. The resolution of the A/D conversion of the data acquisition board was 12 bits. The graphical user interface was designed using the Labview® (National Instrument, Austin, Tex., USA) programming language and digital signal processing methods were developed and tested in Matlab® (The MathWorks, Inc., Natick, Mass., USA).

Methods

Figure 2:
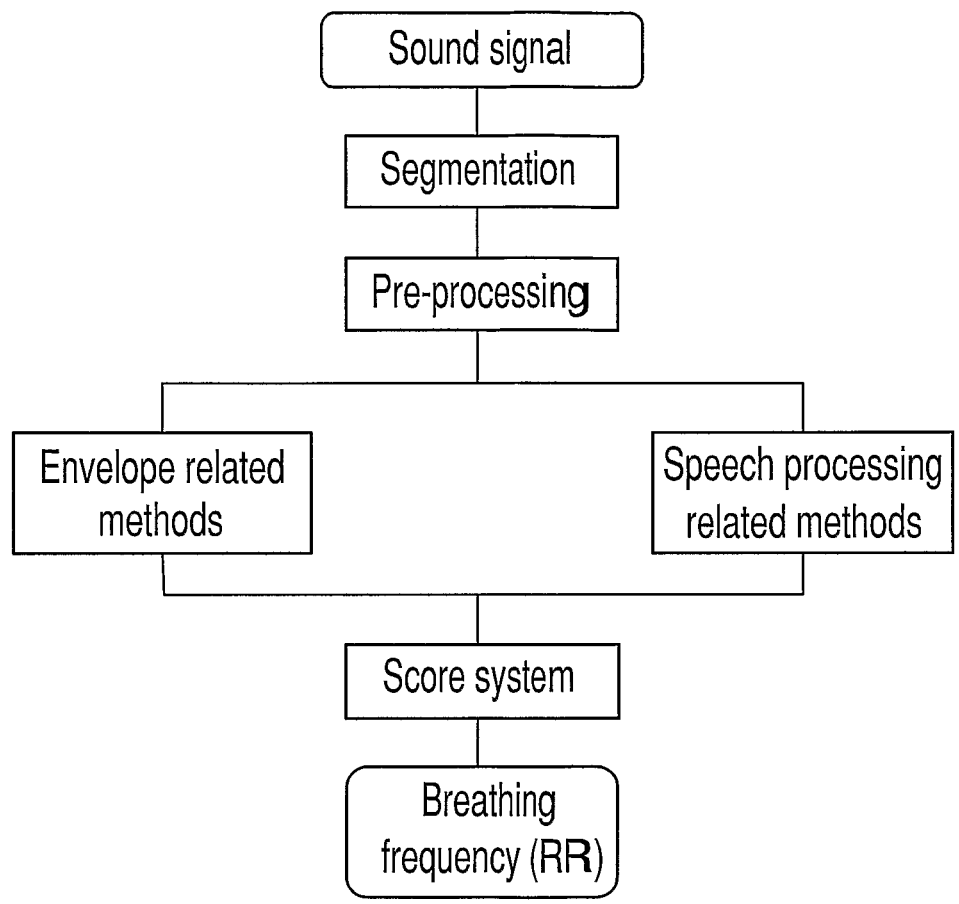
FIG. 2 is a flow chart of a non-invasive respiratory rate, heart rate and apnea monitor according to an illustrative embodiment of the present invention.
Figure 5A:
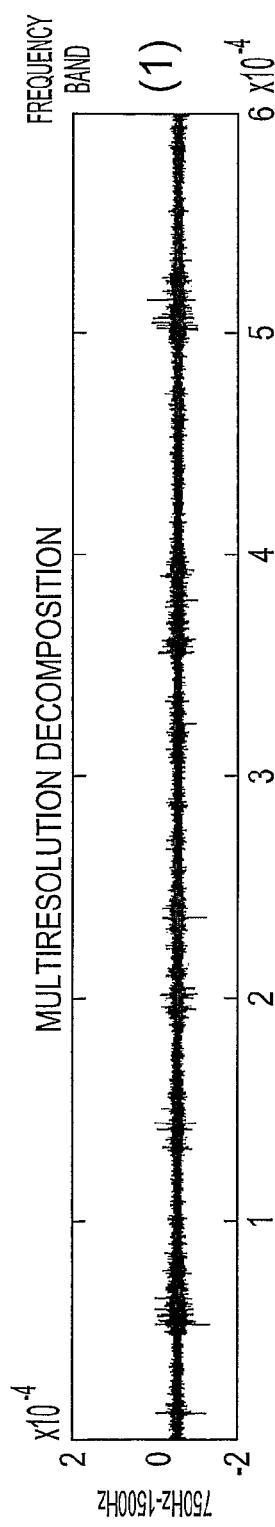
FIG. 5 is a graph of a respiratory sound signal divided into frequency bands according to an illustrative embodiment of the present invention.
Figure 5B:
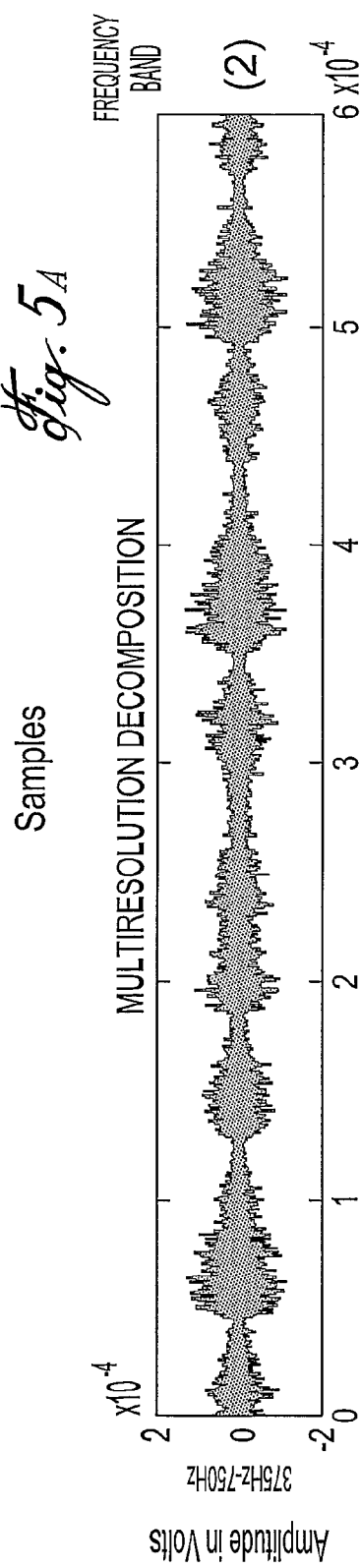
Figure 5C:
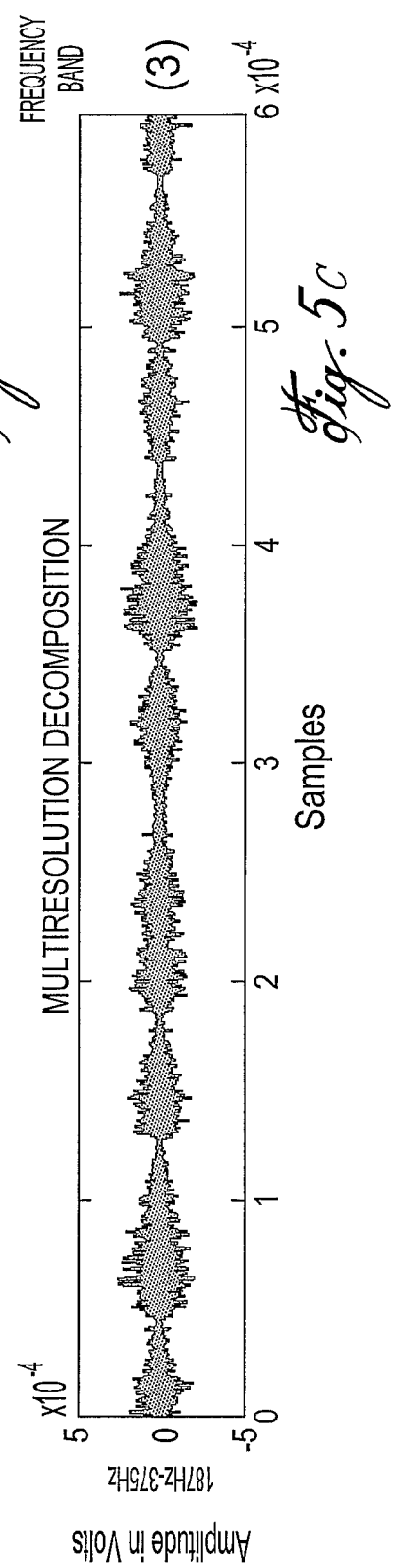
Figure 5D:
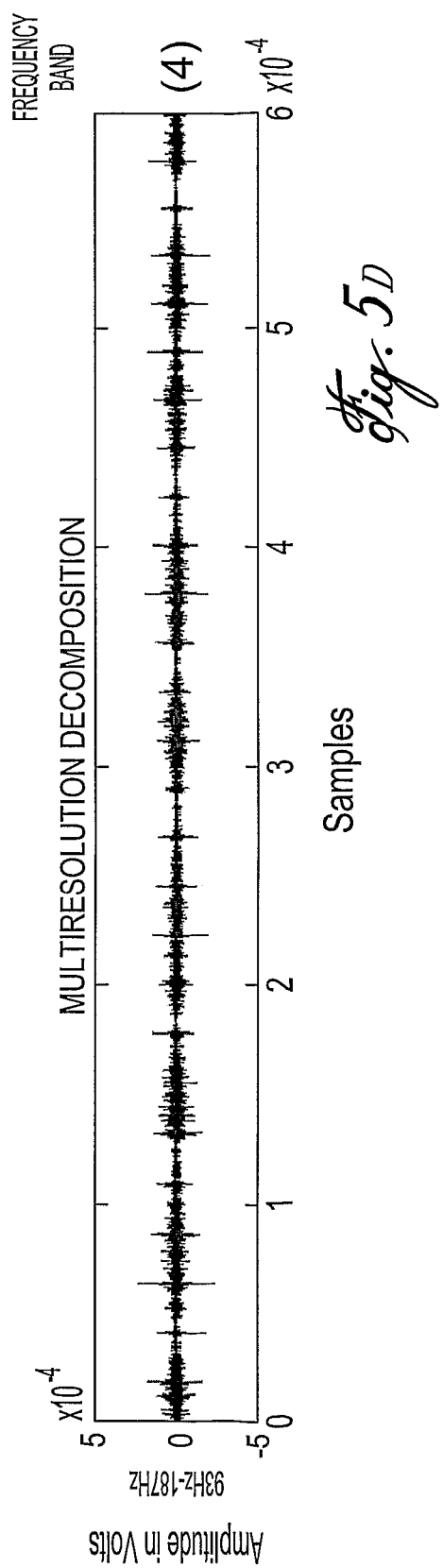
Figure 5E:
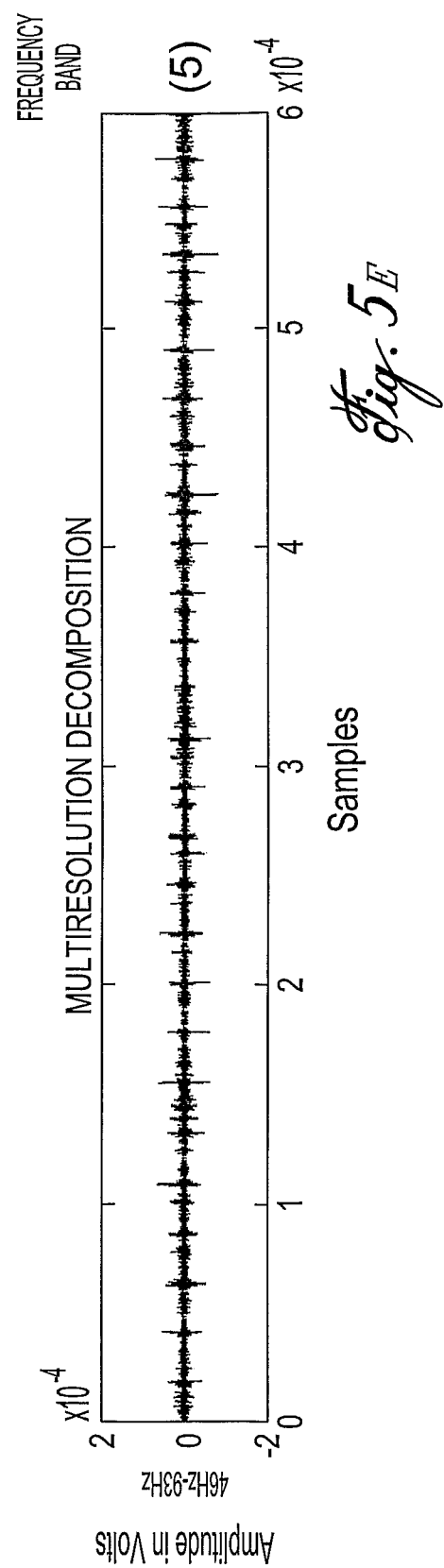

A flow chart indicating the elements of the signal processing method used to estimate the RR from the respiratory tracheal sound signal is provided in FIG. 2 (See also, Sierra G, Telfort V, Popov B, Durand L G, Agarwal R, Lanzo V; *Monitoring Respiratory Rate Based on Tracheal Sounds*, First Experiences; IEEE/EMBS 26th Conferences, San Francisco, Calif., 2004 which is incorporated herein by reference). These elements are described herein below.

Sound Signals and Segmentation Step

The respiratory sound collection is illustratively performed at a sampling frequency of 3000 Hz. For analysis purposes, the sound signal is illustratively segmented into 20 second blocks (although variable block lengths could also be processed) with each block containing five seconds of signal from the previous block (the overlap may also be variable). The breathing frequency is estimated from the sampled 20 seconds of data collection, averaged and displayed every minute.

Pre-processing Step

This step is aimed at ensuring a respiratory sound signal which is as free of interference from internal and external sources of sounds as possible. The following actions are performed during the preprocessing step:

a) A comb-filter is applied to remove the interference from 60 Hz and its harmonics;
b) signals with extremely low signal to noise ratio or high artifacts that saturate the amplifiers are excluded (as will apparent to persons of skill in the art, if saturation occurs, for example when a person talks or cough, signals cannot be processed because the amplifier starts clipping these strong/high amplitude signals. In this case it is preferred to exclude that data segment from analysis. Concerning the case where recordings with extremely low signal to noise ratio exist, they should also be excluded because the signal contribution is almost null due to the masking effect of noises);
c) glitches (or motion artifacts) arising from rubbing clothes on the sensor, intermittent contact, etc., are removed (or attenuated);
d) filtering based on the multi-resolution decomposition (MRD) of a wavelet transform; and
e) removal of strong biological sounds that do not saturate amplifiers but contribute to RR wrong estimation (such strong biological sounds may modify some of the statistical characteristics of the signal being processed, such as maximum amplitude, etc, that are used to detect apnea or low signal to noise ratio.).

Glitch Removal

Referring to FIG. 3, illustratively, the presence of glitches is determined by sampling the respiratory tracheal data. Samples having an amplitude in excess of three times (a value determined as sufficient to identify a large portion of glitches while avoiding capturing other non-glitch signals) the value of the standard deviation are categorized as glitches and removed and replaced by a constant value equal to the amplitude of the sample immediately preceding the removed sample. The mean and standard deviation are illustratively calculated for every one second of signal. The net effect is clipping the signal which means that glitches are not completely removed but rather attenuated. A previous attempt using twice the standard deviation was found to be less effective as an attenuated signal was produced making the estimation process significantly more difficult to accomplish, specially in recordings with low signal to noise ration FIG. 3 shows in the top panel the input signal with scattered glitches and bottom panel after removing some of the glitches.

Multi-Resolution Decomposition (MRD)

Referring to FIG. 4, respiratory sounds (as well as heart sounds) are complicated multi-component non-stationary signals and lend themselves to the use of non-stationary analysis techniques for analyses. MRD allows splitting the respiratory signal into different spectral bands. This decomposition allows for extensive separation of sounds and allows the selection of the best frequency band for processing the respiratory sound signals with the least interference (see FIG. 5).

The frequency range of the above-mentioned frequency bands is determined by the sampling frequency (illustratively Fs=3000 Hz). The output is the filtered signal contained in the frequency bands from 187 Hz to 750 Hz (from 200 Hz to 800 Hz is considered to contain the most important information of the tracheal signal). The MRD approach of the wavelet transform is applied to the respiratory sound signals based on a methodology known in the art for the analysis of different cardiovascular bio-signals. See Sierra G. Fetsch T, Reinhardt L, Martinez-Rubio A, Makijarvi M, Balkenhoff K, Borggrefe M, Breithardt G., *Multiresolution decomposition of the signal-averaged ECG using the Mallat approach for prediction of arrhythmic events after myocardial infarction*, J Electrocardiol 1995, 29:223-234, Sierra G, Reinhardt L, Fetsch T, Martinez-Rubio A, Makijarvi M, Yli-Mayry S. Montonen J. Katila T, Borgrefe M, Breithardt G. *Risk stratification of patients after myocardial infarction based on wavelet decomposition of the signal-averaged electrocardiogram*, Annals of Noninvasive Electrocardiology 1997; 2: 47-58, Sierra G, Gomez M J, Le Guyader P, Trelles F, Cardinal R, Savard P, Nadeau R, *Discrimination between monomorphic and polymorphic ventricular tachycardia using cycle length variability measured by wavelet transform analysis*, J Electrocardiol 1998; 31: 245-255, and Sierra G, Morel P. Savard P. Le Guyader P. Benabdesselam M, Nadeau R., *Multiresolution decomposition of the signal-averaged ECG of postinfarction patients with and without bundle branch block*, Proceedings of the 18th Annual International Conference of the IEF Engineering in Medicine and Biology Society, Amsterdam, Oct. 31-Nov. 3, 1996, all incorporated herein by reference The MRID approach to wavelet transform allows noise to be removed from the input signals and the biological sounds to be separated into different frequency bands. As is known in the art, a variety of wavelet families exist, one or more of which may be appropriate in a particular application. No established rules exist on how to evaluate the most suitable wavelet family for a specific application. Illustratively, the 'Coifflet' wavelet family was used although other wavelet families, such as Lemarie-Battle and Symlet may in some implementations be preferable.

Illustratively, the original signal is decomposed into ten (10) frequency bands: 750 Hz-1500 Hz, 375 Hz-750 Hz, 187 Hz-375 Hz, 93 Hz-187 Hz, 46 Hz-93 Hz, 23 Hz-46 Hz, 12 Hz-23 Hz, 6 Hz-12 Hz, 3 Hz-6 Hz and from DC to 3 Hz. As mentioned above, the range of these bands is determined by the sampling frequency (in the case at hand Fs=3000 Hz although a person of skill in the art would understand that a higher or lower sampling rate could be used). An illustrative example of the amplitudes of the samples in the first five (5) frequency bands is shown in FIG. 5. Referring to FIG. 5, frequency bands two (2) and three (3) carry the most important information to estimate respiratory rate. Frequency bands four (4) and five (5) show clearly information related to a beating heart.

The estimation of RR is hindered by several factors such as the non-stationarity and non-linear nature of the respiratory sound signal, the interference of non-biological (60 Hz, environment noise, glitches, etc) and biological signals (heart beat, swallow, cough, speech and others) and recordings with low signal to noise (S/N) ratio. Another problem arises when one of the respiratory phases is significantly stronger than the other and abnormal patterns, for example those which are the result of certain pulmonary diseases, although abnormal patterns are also present in some individuals without these diseases.

As discussed above, apnea is a temporary cessation of the respiratory function. The most widely used criterion as an indication of apnea is 10 seconds or greater of duration for the cessation. In the present proposed method, the duration, or time threshold, of cessation of respiratory function indicating apnea is a configurable parameter. Once the peaks in the envelope signal are being detected, the time interval between two consecutive peaks is estimated and compared with the configured time threshold. If it is greater than the threshold, apnea is flagged as having been detected and an alarm raised.

A special type of apnea occurs when no envelope peaks are detected. To discriminate apnea from a 'sensor disconnected' we use the power spectrum analysis. While the sensor is connected to the patient the low biological frequencies (frequencies with higher power values in the band from 200 Hz to 300 Hz) will prevail. If the sensor is disconnected higher frequencies (frequencies with high power values over 500 Hz) will prevail. Additionally, to be certain that no envelope peaks exist, both the root mean squared (RMS) value of the envelope and an envelope history of the previous one minute of signal are retained. If a significant drop of amplitude happens in the 20 sec segment (to less than 12% of the RMS value), then apnea is detected.

In order to overcome the difficulties found when using a single method to produce an estimation of RR with high accuracy, a multiple technique approach is used. As a result, the pre-processed signals are analyzed using both envelope-based and speech-processing related methods as described in more detail herein below.

Envelope Related Methods for Estimating Respiratory Rate

The respiratory sound signal acquired on the tracheal site can be modeled as sinusoidal signals from 200 Hz to 800 Hz modulated by a slow oscillatory signal that represents inspiratory and expiratory envelopes. Illustratively, the envelope is obtained based on a Hilbert transform and decimation of the wavelet filtered sound signal (from 187 Hz to 750 Hz) in a proportion of fifty to one. The envelope is a very low frequency signal that modulates those components of the respiratory sounds located in the band from 187 Hz to 750 Hz. In this regard, decimation means that the envelope signal (obtained with the Hilbert transform) is down sampled to have less data points to process and thus decrease the execution tire targeting real-time applications. For example, a respiratory sound sampled at 3 kHz for a duration of 20 seconds corresponds to 60000 data points, which when down sampled is only 1200 data points. The low frequency envelope is detected, followed by the determination of its oscillatory period. Based on this period (time lags between consecutive inhalations or exhalations) the RR that would be accounted for after one minute has elapsed is estimated.

Estimating Respiratory Rate Based on the Fast Fourier Transform (FFT).

The power spectrum is estimated from the detrended and windowed (Hanning) envelope signal based on a nonparametric fast Fourier transform (FFT). The magnitude squared of the FFT coefficients formed the power spectrum. Once the envelope is represented in the frequency domain, typically the component with the second highest peak has the information to correctly estimate the RR result.

Estimating Respiratory Rate Based on Envelope Counting

In order to estimate RR based on envelope counting, all possible peaks in the envelope signal of the respiratory sound signal are identified and then the RR computed as a function of the time between consecutive inhalations or exhalations enclosed in the selected segment.

All possible peaks are detected by an analysis of samples that fulfil a criterion of local maximum plus a criterion of stability (amplitude higher than a number of samples before and after the peak, see FIG. 6). In this regard, all peaks detected within a given frame of the signal (illustratively 20 seconds but other lengths are also possible) are passed through heuristic validation method. This validation method selects only the peaks higher than 10% of the amplitude of the higher peak on the given signal. A rule of minimal possible distance between two consecutive peaks is also used. Once all peaks have been determined, the mean of the difference of consecutive odd peaks included in the data segment (illustratively of 20 seconds in length) is calculated. The inverse of this value multiplied by 60 equals the estimation of RR.

Estimating Respiratory Rate Eased on the Autocorrelation Function

The autocorrelation function exploits the fact that a periodic signal, even if it is not a pure sine wave, will be similar from one period to the next. This is true even if the amplitude of the signal is changing in time, provided those changes do not occur too rapidly. Once the autocorrelation function is obtained, the first two peaks are analyzed to select the one with the RR information. Typically, the second peak is the correct choice (but this is not always so). Samples where one respiratory phase was more accentuated than the other and some other cases were better estimated by the first peak.

Estimating Respiratory Rate Based on Wavelet Transform

The appropriate frequency band to be selected for RR analysis changes according to the actual RR. Therefore guidance is required for the right band selection. This guidance is provided by the RR result of the FFT analysis, which allows choosing typically two, or exceptionally three, possible frequency bands. In these bands, the selection of peaks (based on maxima and minima analyses) and the estimation of RR (two or three) is performed similarly as explained in the method of envelope counting. Finally, the RR closest to the RR estimated by the FFT is taken as the RR estimated by the wavelet method.

Speech Processing Related Methods for Estimating Respiratory Rate

The speech processing approach was used to overcome some limitations of the methods that dealt directly with determining the envelope of the respiratory signal, particularly in low S/N ratio recordings. By combining methods based on the envelope and methods based on the respiratory signal, a better estimation of the RR can be achieved.

Figure 7:
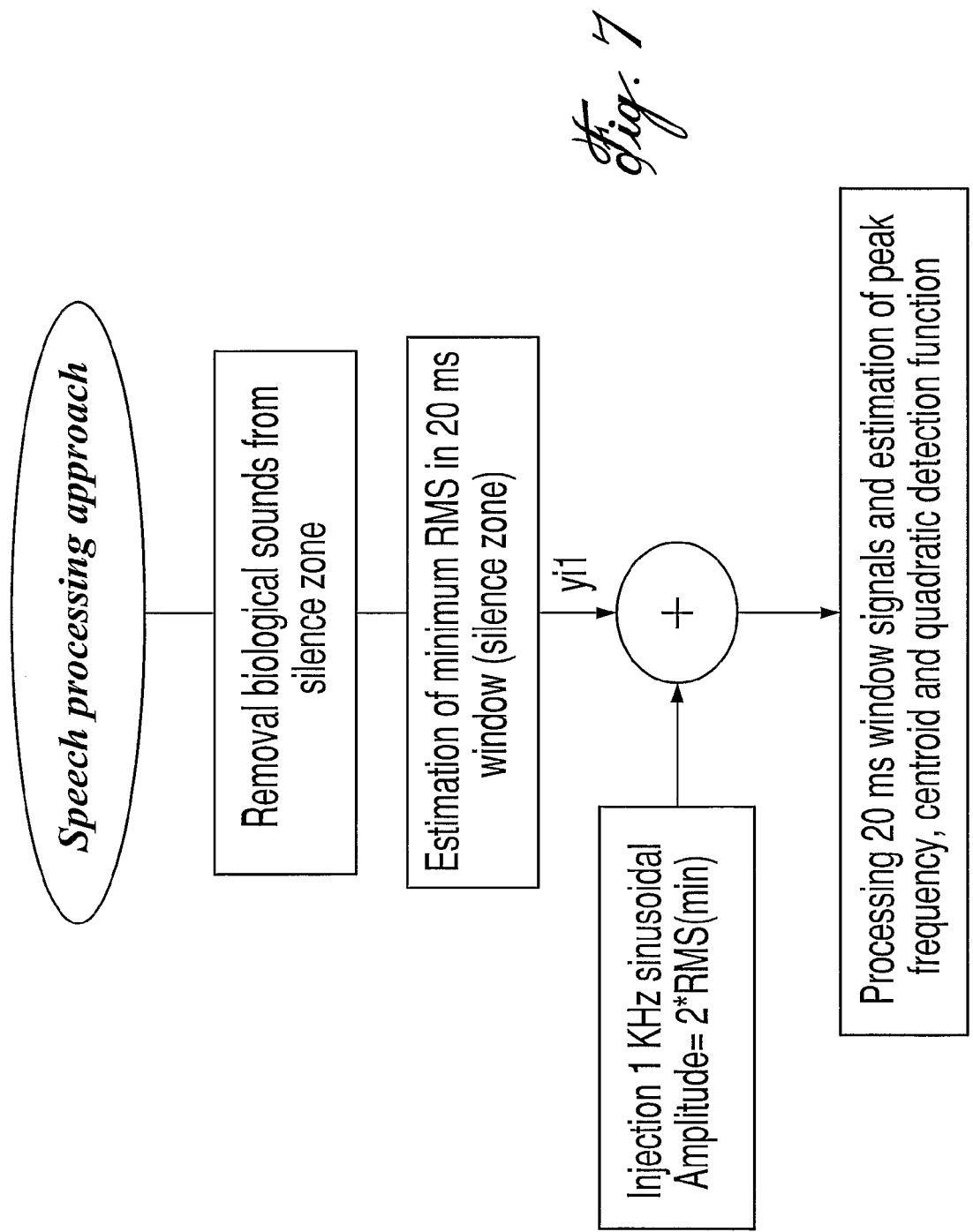
FIG. 7 is a flow chart of speech processing method according to an illustrative embodiment of the present invention.

Using the speech processing approach, relevant information of the signal under analysis is acquired through the processing of small segments of signals (20 ms duration in this case) where the statistical properties of the signal are assumed to remain stable (stationarity). The analysis is performed in the frequency domain and the main tool is a short-time FFT technique. The flowchart of FIG. 7 illustrates the approach.

The speech processing approach faces some challenges due to the fact that there are no clear spectral differences between inhalation and exhalation phases recorded at the tracheal site. To overcome these limitations, a pilot signal with a frequency (for example, 1 kHz) which is out of the frequency range of interest (200 Hz to 800 Hz), and having an amplitude at least twice the minimum RMS of the respiratory signal is combined with the respiratory signal. During intervals of silence between inhalation and exhalation (i.e. where there is an absence of any respiratory sounds) the pilot signal prevails. Likewise, during inhalation/exhalation phases the respiratory signal prevails. As a result, detection of the pilot signal gives an indication of a silence interval An additional measure to help accentuate the difference between respiratory signal and silence is the removal (or attenuation) of biological sounds within the silence interval. This function removes or attenuates biological sounds (mainly heart sounds) found in the silence interval and that were not considered glitches in the pre-processing stage. This processing is based on an adaptive filter technique that takes the respiratory signal contaminated with the heart sounds in a first channel (from 100 to 1500 Hz) and the heart sounds from a second channel (from 1 to 30 Hz, both channels simultaneously recorded) and produces as output a respiratory signal 'free' of heart interferences. Respiratory signals combined with the 1 kHz pilot signal provide the input. A FFT is applied to windows of 20 ms and parameters such as power (FFT magnitude squared), centroid (frequency multiplied by power divided by power) and a quadratic detection function (squared frequency multiplied by power) are estimated. All these parameters are used as RR estimators.

Figure 8A:
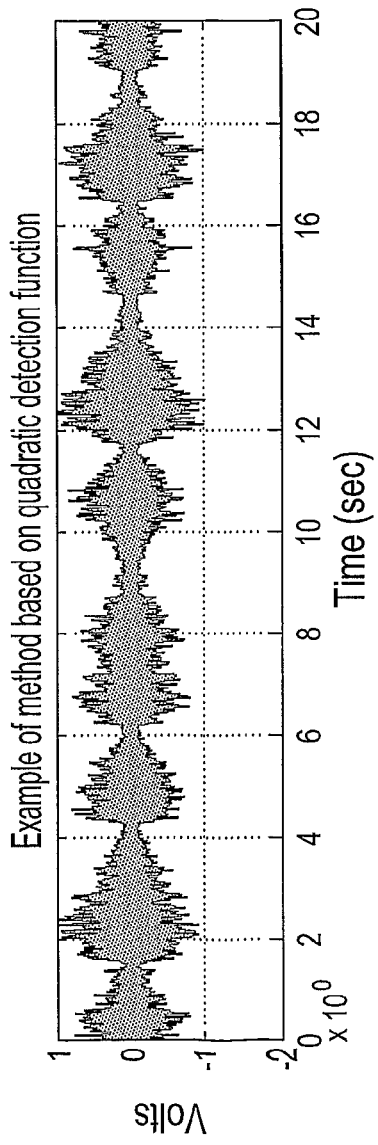
FIG. 8 is a graph of an example of a method based on a quadratic detection function of the speech processing method according to an illustrative embodiment of the present invention.
Figure 8B:
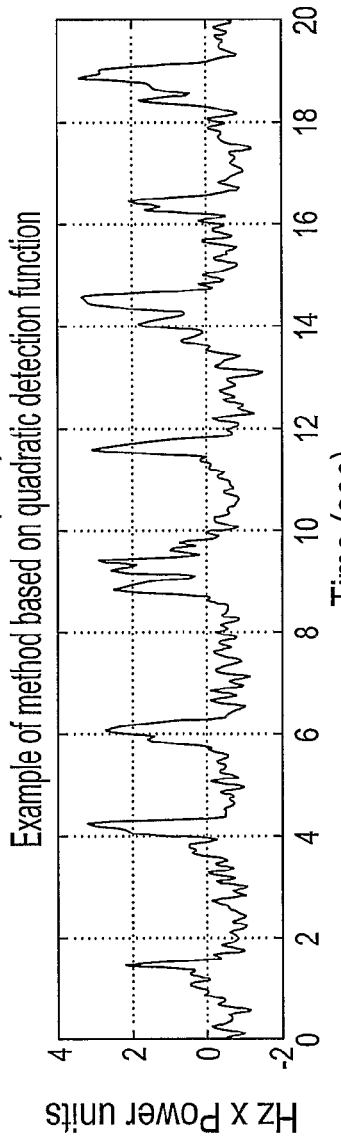
Figure 8C:
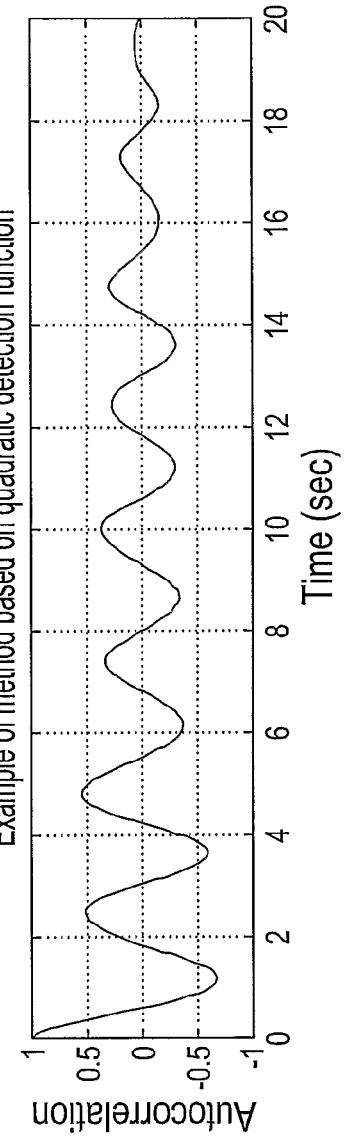

As an illustration, FIG. 8 displays on the top panel a pre-processed respiratory sound signal. The middle panel shows a signal produced by the quadratic detection function with peaks indicating the position of zones of silence. The bottom panel represents the autocorrelation function of the signal in the middle panel. The second peak of the autocorrelation is used to estimate the RR.

Finally, a scoring system, comprising a heuristically-based analysis of the individual estimators, is applied to determine the final RR based on the results of the individual estimators.

Scoring System

The final respiratory rate (FR) for a particular segment is determined as a function of the RR as determined by each of the individual estimators (as discussed hereinabove) as well as the final respiratory rate of the previous segment (FR Old).

In an illustrative embodiment, the individual estimators are examined and if there is one value of RR which is predominant, FR is set to the predominant RR value. If no value of RR is predominant, but two or three values have equal representation, then the value which is closest to FR Old is selected. Finally, if more than three values have equal representation FR is set to the same value as FR Old.

Heart Rate

Heart sounds are also present among the sounds captured on the trachea site. For the estimation of the respiratory rate they are considered as 'noise' and are removed. However, these sounds allow the possibility of estimating heart rate (one of the most important vital signs) easily. We have implemented a second hardware channel with filter settings (20-200 Hz) to enhance the detection of heart sounds and reject all other biological sounds (including respiratory). Applications involving the cardio-respiratory interactions, regulation of the autonomous nervous system on the cardiovascular system and others will be easily targeted. Once the heart sounds are filtered, sound peaks are detected. Based on the inter-peaks timing the heart rate is estimated (beats per minute).

Although the present invention has been described hereinabove by way of an illustrative embodiment thereof, this embodiment can be modified at will, within the scope of the present invention, without departing from the spirit and nature of the subject of the present invention.

What is claimed is:

1. A method for estimating a respiratory rate of a patient comprising the steps of: receiving respiratory sound data representing respiratory sounds of the patient; deriving a plurality of respiratory rates from said respiratory sound data with a processor using a plurality of different respiratory rate estimating methods, wherein the plurality of different respiratory rate estimating methods comprises a plurality of envelope related methods, at least one of the envelope related methods being performed in a time domain and at least another of the envelope methods being performed in a frequency domain; and applying a heuristic to said plurality of derived respiratory rates, said heuristic selecting one of said derived respiratory rates to output for display to a clinician; wherein said selected respiratory rate is the estimated respiratory rate.

2. The method of claim 1, wherein said respiratory sounds are recorded at the patient's trachea.

3. The method of claim 1, wherein said recording step comprises sampling said respiratory sounds at a predetermined sampling rate.

4. The method of claim 1, wherein one of said envelope related methods comprises obtaining a low frequency envelope of said recorded sounds and determining a period of time of said envelope.

5. The method of claim 4, wherein said low frequency envelope is obtained by at least applying a Hilbert transform to said recorded sounds.

6. The method of claim 1, wherein said envelope related methods comprise one or more of the following: a Fast Fourier Transform (FFT) power spectrum method, an envelope counting method, an autocorrelation method and a wavelet transform method.

7. The method of claim 6, wherein said respiratory sounds are recorded for a predetermined time interval using a sampling method and wherein said FFT power spectrum method comprises transforming said sampled sounds into a series of discrete frequency bands using an FFT, generating a power spectrum from said series of discrete frequency bands, and selecting said discrete frequency band having the second greatest amplitude within the predetermined time interval, wherein said derived respiratory rate is equal to a frequency of said selected frequency band.

8. The method of claim 6, wherein said respiratory sounds are recorded for a predetermined time interval using a sampling method and wherein said envelope counting method comprises identifying peaks in said low frequency envelope and determining a mean difference in amplitude of consecutive odd peaks in said predetermined interval, wherein said derived respiratory rate is proportional an inverse of said mean difference.

9. The method of claim 8, wherein said peaks are identified by selecting samples which fulfill a local maximum criterion and a stability criterion.

10. The method of claim 6, wherein said respiratory sounds are recorded for a predetermined time interval using a sampling method and wherein said autocorrelation method comprises generating an autocorrelation function from said sampled respiratory sounds, wherein said derived respiratory rate is equal to a first peak of said autocorrelation function.

11. The method of claim 6, wherein said respiratory sounds are recorded for a predetermined time interval using a sampling method and wherein said autocorrelation method comprises generating an autocorrelation function from said sampled respiratory sounds, wherein said derived respiratory rate is equal to a second peak of said autocorrelation function.

12. The method of claim 6, wherein said respiratory sounds are recorded for a predetermined time interval using a sampling method and wherein said wavelet transform method comprises transforming said sampled sounds into the frequency domain using an FFT, dividing said transformed sounds into a plurality of frequency bands, selecting two frequency bands, determining an estimated rate for each of said selected bands using an envelope method and selecting one of said estimated rates, wherein said derived respiratory rate equals said selected rate.

13. The method of claim 6, wherein said respiratory sounds are recorded for a predetermined time interval using a sampling method and wherein said wavelet transform method comprises transforming said sampled sounds into the frequency domain using an FFT, dividing said transformed sounds into a plurality of frequency bands, selecting three frequency bands, determining an estimated rate for each of said selected bands using an envelope method and selecting one of said estimated rates, wherein said derived respiratory rate equals said selected rate.

14. The method of claim 3, further comprising a segmentation step prior to said deriving step.

15. The method of claim 10, wherein said segmentation step comprises dividing said sampled sounds into blocks of samples over a time interval.

16. The method of claim 15, wherein said interval is between 10 and 30 seconds.

17. The method of claim 15, wherein said time interval is variable.

18. The method of claim 15, wherein each of said time intervals includes a portion of a time interval immediately prior to said time interval.

19. The method of claim 18, wherein said prior time interval portion is between 0 seconds and a duration of said time interval.

20. The method of claim 1, further comprising a preprocessing step prior to said deriving step.

21. The method of claim 20, wherein said preprocessing step comprises removing artifacts from said respiratory sounds.

22. The method of claim 21, wherein said artifact removing step comprises identifying recorded sounds having an amplitude greater than three times the standard deviation of a predetermined time interval of said recorded respiratory sounds.

23. The method of claim 22, wherein said predetermined time interval is one second prior to said identified sound.

24. The method of claim 20, wherein said preprocessing step comprises filtering said recorded sounds using a comb filter.

25. The method of claim 24, wherein said comb filter attenuates recorded sounds having a frequency of 60 Hz and harmonics of 60 Hz.

26. The method of claim 20, wherein said preprocessing step comprises attenuating recorded noise sounds with low signal to noise ratio.

27. The method of claim 20, wherein said preprocessing step comprises removing recorded sounds with artifacts that saturate the amplifiers.

28. The method of claim 20, wherein said preprocessing step comprises filtering using multi-resolution decomposition (MRD) of a wavelet transform.

29. The method of claim 28, wherein said wavelet transform is selected from the Coifflet family of wavelet transforms.

30. The method of claim 20, wherein said preprocessing step comprises attenuating strong recorded noise sounds that do not saturate amplifiers but contribute to respiratory rate (RR) wrong estimation.

31. The method of claim 28, wherein said MRD filtering step comprises dividing said recorded sounds into a plurality of spectral bands, identifying a frequency range of interest and removing recorded sounds not in spectral bands in said identified frequency range of interest.

32. The method of claim 31, wherein said identified frequency range of interest is between 200 Hz and 800 Hz and said spectral bands comprise the band of 750 Hz-1500 Hz, the band of 375 Hz-760 Hz, the band of 187 Hz-375 Hz, the band of 93 Hz-187 Hz, the band of 46 Hz-93 Hz, the band of 23 Hz-46 Hz, the band of 12 Hz-23 Hz, the band of 6 Hz-12 Hz, the band of 3 Hz-6 Hz and the band of DC to 3 Hz.

33. The method of claim 1, wherein said heuristic applying step comprises examining said plurality of derived respiratory rates, wherein said selected respiratory rate is a predominant one of said derived respiratory rates, wherein in the event there is no predominant derived respiratory rate but two or three of said derived rates have equal representation, then said selected respiratory rate is said derived respiratory rate closest to a previous estimated respiratory rate, and wherein if more than three of said derived rates have equal representation, said selected respiratory rate is equal to said previous estimated respiratory rate.

34. A method for signaling sleep apnea comprising the steps of: the method according to claim 1, wherein when said estimated respiratory rate exceeds a predetermined time interval an alarm is raised.

35. The method of claim 34, wherein said predetermined interval is between 10 and 30 seconds.

36. An apparatus for providing an estimated respiratory rate of a patient, the apparatus comprising:
one or more processors, the one or more processors configured to:
receive respiratory sound data representing respiratory sounds of a patient;
calculate respiratory rates based on the respiratory sound data using a plurality of envelope related methods, at least one of the envelope related methods comprising a time domain method and at least another of the envelope related methods comprising a frequency domain method; and select one of said calculated respiratory rates to output as an estimated respiratory rate for display to a clinician.

37. The apparatus of claim 36, further comprising a display for displaying the estimated respiratory rate.

* * * * *

UNITED STATES PATENT AND TRADEMARK OFFICE
CERTIFICATE OF CORRECTION

| | | |
|---|---|---|
| PATENT NO. | : 8,641,631 B2 | Page 1 of 1 |
| APPLICATION NO. | : 11/547570 | |
| DATED | : February 4, 2014 | |
| INVENTOR(S) | : Sierra et al. | |

It is certified that error appears in the above-identified patent and that said Letters Patent is hereby corrected as shown below:

In the Specification

In column 1 at line 30, change "A," to --L,--.

In column 1 at line 57, change "68)" to --58)--.

In column 2 at line 34, change "heart seat," to --heart beat,--.

In column 6 at line 25, change "ration" to --ratio.--.

In column 6 at line 53, change "Borgrefe" to --Borggrefe--.

In column 6 at line 65, change "IEF" to --IEEE--.

In column 6 at line 67, change "reference" to --reference.--.

In column 7 at line 1, change "MRID" to --MRD--.

In column 8 at line 50, change "Eased" to --Based--.

In column 9 at line 34, change "interval" to --interval.--.

Signed and Sealed this
Ninth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,641,631 B2
APPLICATION NO. : 11/547570
DATED : February 4, 2014
INVENTOR(S) : Sierra et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1712 days.

Signed and Sealed this
Twenty-first Day of July, 2015

Michelle K. Lee
*Director of the United States Patent and Trademark Office*